United States Patent
Alving et al.

[11] Patent Number: 6,110,492
[45] Date of Patent: Aug. 29, 2000

[54] IMMUNOGENIC COMPOSITIONS

[75] Inventors: Carl R. Alving, Bethesda; Jean M. Muderhwa, Silver Spring, both of Md.; Lynn E. Spitler, Tiburon, Calif.

[73] Assignee: Jenner Biotherapies, Inc., San Ramon, Calif.

[21] Appl. No.: 09/086,552

[22] Filed: May 28, 1998

Related U.S. Application Data

[60] Provisional application No. 60/047,964, May 28, 1997.

[51] Int. Cl.[7] .................................................... A61K 9/127
[52] U.S. Cl. .......................................... 424/450; 436/829
[58] Field of Search ..................................... 424/450, 94.3, 424/1.21, 9.321, 9.51, 417; 514/947; 436/829; 935/54; 428/402.2

[56] References Cited

U.S. PATENT DOCUMENTS

| | | |
|---|---|---|
| 3,957,971 | 5/1976 | Oleniacz . |
| 5,055,228 | 10/1991 | Zabotto et al. . |
| 5,256,422 | 10/1993 | Albert et al. . |
| 5,439,672 | 8/1995 | Zabotto et al. . |
| 5,489,426 | 2/1996 | Zabotto et al. . |
| 5,709,879 | 1/1998 | Barchfeld ................................. 424/450 |

FOREIGN PATENT DOCUMENTS

| | | |
|---|---|---|
| 0 043 327 | 6/1981 | United Kingdom . |
| 2 079 179 | 1/1982 | United Kingdom . |
| 92/17179 | 10/1992 | WIPO . |
| 93/10763 | 6/1993 | WIPO . |

OTHER PUBLICATIONS

XP-002090030, G. Vanlerberghe, "Dispersed Lyotropic Phases as Carriers for Active Substances," Nuovo Cimento Soc. Ital. Fis., vol. D, No. 3D1, 1984, pp. 219–233.
A Non–Ionic Surfactant Vesicle–in–Water–in–Oil (v/w/o) system: Potential Uses in Drug and Vaccine Delivery, toshimitsu Yoshioka et al., *Journal of Drug* Targeting, 1995, vol. 2, pp. 533–539.
Liposomes as Carriers for Vaccines, Nabila M. Wassef, et al., *Immunomethods*, 4:217–222 (1994).

*Primary Examiner*—Gollamudi S. Kishore
*Attorney, Agent, or Firm*—Morrison & Foerster LLP

[57] ABSTRACT

A composition which comprises a stable oil-in-water emulsion having a continuous water phase and a discontinuous oil phase and containing, as sole stabilizing agent, a sufficient quantity of smectic mesophase vesicles and their disintegrated forms to provide at least about 100 mM amphiphile is stable and useful as an adjuvant, in a vaccine, or drug delivery system

15 Claims, 19 Drawing Sheets

CLINICAL TRIAL #1
IM ADMINISTRATION OF ONCO VAX-P™
FEBRUARY 6, 1998

| PATIENT | AGE | PRIOR TREATMENT | SITES | VACCINE | PSA Pre | PSA D 90 | CLIN RESP | PSA LAST | POST | LAST FU | DEATH |
|---|---|---|---|---|---|---|---|---|---|---|---|
| 1. A W (#001) | 63 | HORMONAL SURGERY RADIATION | BONE | 9/95-12/95 5/96-8/96 11/96-12/96 4/97-10/97 | 5.64 | 5.77 | S | 10.66 10/97 | | 2/98 | |
| 2. J H (#002) | 72 | RADIATION SURGERY ORCHIECTOMY HORMONAL | BONE | 10/95-1/96 1/97-5/97 | 34.0 | | PD/S | 192 9/97 | PD 6/97 | 1/98 | |
| 3. M D (#003) | 73 | ORCHIECTOMY HORMONAL | BONE | 11/95-2/96 | 25.98 | 338.5 | PD | 338 2/96 | | | 6/96 |
| 4. M ED (#004) | 52 | HORMONAL | LOCAL | 11/96-2/96 | 16.70 | 27.53 | PD | 55 12/96 | XRT, CHEMO 1/97 | | 5/97 |
| 5. H N (#005) | 48 | SURGERY HORMONAL RADIATION | NODAL, BONE | 2/96-5/96 | 4.25 | 75.57 | PD | | | | 2/97 |
| 6. J LB (#006) | 78 | ORCHIECTOMY HORMONAL RADIATION | LOCAL, BONE | 3/96-6/96 | 10.76 | 17.87 | S | 111 11/96 | | | 1/97 |

FIG. 7

CLINICAL TRIAL #2
ADMINISTRATION OF ONCO VAX-P™ EMULSION
FEBRUARY 6, 1998

| PATIENT | AGE | PRIOR TREATMENT | SITES | VACCINE | PSA Pre | PSA D 90 | CLIN RESP | PSA LAST | POST | LAST FU | DEATH |
|---|---|---|---|---|---|---|---|---|---|---|---|
| 1. PL (#401) | 67 | BIOPSY ORCHIECTOMY HORMONAL | PROSTATE BONE | 8/97-11/97 1/98 | 0.98 | 0.31 | S | <0.05 (1/98) | BOOST | 1/98 | |
| 2. ET (#402) | 70 | BIOPSY HORMONAL | PROSTATE BONE | 8/97-11/97 1/98 | 46.3 | 525.80 | IMPROVED BONE SCAN* | 1622.40 (1/98) | BOOST | 1/98 | |
| 3. DT (#403) | 74 | BIOPSY RADIATION HORMONAL | PROSTATE | 8/97-11/97 1/98 | 9.91 | 13.55 | S | 6.51(1/98) | BOOST | 1/98 | |
| 4. HV (#404) | 70 | BIOPSY RADIATION HORMONAL | PROSTATE BONE | 9/97-12/97 | 18.13 | 51.46 | S | | BOOST | 12/97 | |
| 5. JG (#405) | 75 | BIOPSY RADIATION | PROSTATE | 9/97-12/97 | 35.40 | 39.91 | S | | | 12/97 | |

*ALKALINE PHOSPHATASE 1200→300

FIG.8

IMMUNOGENIC COMPOSITIONS

This is a Continuation of the Provisional Application No. 60/047,964 filed on May 28, 1997.

FIELD OF THE INVENTION

The invention relates to emulsion technology, especially as it pertains to vaccines and therapeutic compositions. More specifically, the invention concerns a vesicle-stabilized oil-in-water emulsion that can be used as an adjuvant for vaccines or as a carrier for immunogens or therapeutic substances.

BACKGROUND ART

Incomplete Freund's Adjuvant (IFA) is an emulsion-based adjuvant that has been widely used. It is a water-in-oil emulsion consisting of a light paraffinic mineral oil of low viscosity that is stabilized by Arlacel™ mannide monooleate as a stabilizing emulsifier. IFA has been administered as an adjuvant to more than a million persons worldwide as a constituent in influenza, poliomyelitis, cholera, typhoid and tetanus toxoid vaccines. Although this adjuvant appears very safe, a small number of those administered vaccines containing IFA showed toxic reactions, and hence efforts have been made to find suitable substitutes.

Other emulsion-based adjuvants have thus been developed. Among these is the Syntex Adjuvant Formulation (SAF) which utilizes a detergent as an emulsifier.

Besides their ability to act as adjuvants, emulsions are also important in formulating cosmetics, and emulsions are often found among food products, such as mayonnaise; however, the present invention is directed to emulsions useful to deliver immunogens or antigens, as well as therapeutic substances.

Emulsions are stabilized suspensions either of oil in water (o/w, i.e., water is a continuous phase with oil as a discontinuous phase) or water in oil (w/o, wherein water is a discontinuous phase and oil is a continuous phase). In both, the oil and water phases are prevented from separating by addition of an emulsifier. Emulsifiers are "amphiphiles" or amphipathic molecules containing a hydrophobic region and a hydrophilic region. Typical examples are detergents and phospholipids, such as lecithins.

It is not unknown to include vesicles such as liposomes in or as emulsions for various purposes. For example, such preparations are described in U.S. Pat. No. 3,957,971; UK patent GB 2,079,179; and U.S. Pat. No. 5,256,422. It appears that the '971 and '179 patents relate to liposomal compositions per se; thus, the emulsions are those of liposomes themselves in an aqueous suspension. This '422 patent relates to w/o emulsions. In all cases, an emulsifier is added to the preparation in addition to the liposomes. Yoshioka, T. el al., *J Drug Targeting*(1995) 2:533–539, similarly, disclose a water-in-oil emulsion containing nonionic surfactant vesicles (niosomes) which employs an additional emulsifying agent. In the Yoshioka paper, the same molecule was used to provide the amphiphilic component of the vesicles as was also used for the emulsifier.

Vesicles have been used alone to stabilize cosmetic emulsions. U.S. Pat. Nos. 5,489,426 and 5,439,672 describe oil-in-water emulsions stabilized by niosomes—i.e., vesicles similar to liposomes formed from nonionic amphiphiles (further described below), although ionic amphiphiles may be included as well. The oil phase in these compositions is a fatty acid ester. The niosomes are said not only to stabilize the emulsion, but to exhibit stability themselves in the context of the emulsion. U.S. Pat. No. 5,055,228 describes oil-in-water emulsions for a variety of uses that are stabilized by the presence of vesicles, which vesicles may contain either ionic or nonionic amphiphiles or both. A major advantage of this composition is said to be the enhanced stability of the vesicles due to the presence of oil droplets. After formation of an illustrative emulsion (column 6) 36% of the glucose entrapped in the vesicles was released after 5 days, while a similar dispersion lacking oil droplets released 45% of the glucose contained in the vesicle after 5 days.

Liposomes per se have also been used as carriers in vaccines. See, for example, PCT application WO 93/10763. In one particular application, the adjuvant is an amphipathic lipid which becomes incorporated into the liposomes per se. See Wassef, N. M. et al., *Immunomethods* (1994) 4:217–222.

There remains a need to add to the repertoire of emulsions that can be used adjuvants, vaccines, and the like without negative reactions on the part of subjects administered them and with maximal ability to stimulate a desired therapeutic or immune response. The present invention provides such compositions.

DISCLOSURE OF THE INVENTION

The invention relates to new compositions which are stable oil-in-water (o/w) emulsions using, as sole stabilizing agent, a sufficient quantity of vesicles (including their disintegrated forms), which vesicles further contain immunogens or therapeutic substances, and the like. The invention also relates to methods to prepare and use these compositions.

Thus, in one aspect, the invention is directed to a pharmaceutical or veterinary formulation which comprises a stable oil-in-water emulsion having a continuous water phase and a discontinuous oil phase and containing, as sole stabilizing agent, smectic mesophase vesicles and disintegrated forms thereof, wherein said vesicles encapsulate at least one therapeutically active ingredient and provide 90 mM–140 mM amphiphile in said composition.

In another aspect, the invention is directed to preparing the emulsions of the invention by applying shear forces to mix the oil phase with vesicle-containing aqueous phase.

BRIEF DESCRIPTION OF THE DRAWINGS

FIG. 4a shows results when the emulsion was made by vortexing; FIG. 4b when made by applying shear forces.

FIG. 7 is a chart showing the treatment and status of 6 individual patients administered a liposomal composition which is not emulsified containing PSA.

FIG. 8 is a chart showing similar parameters with respect to 5 other patients administered liposomal PSA formulated as the emulsion of the invention.

MODES OF CARRYING OUT THE INVENTION

Figure 1:
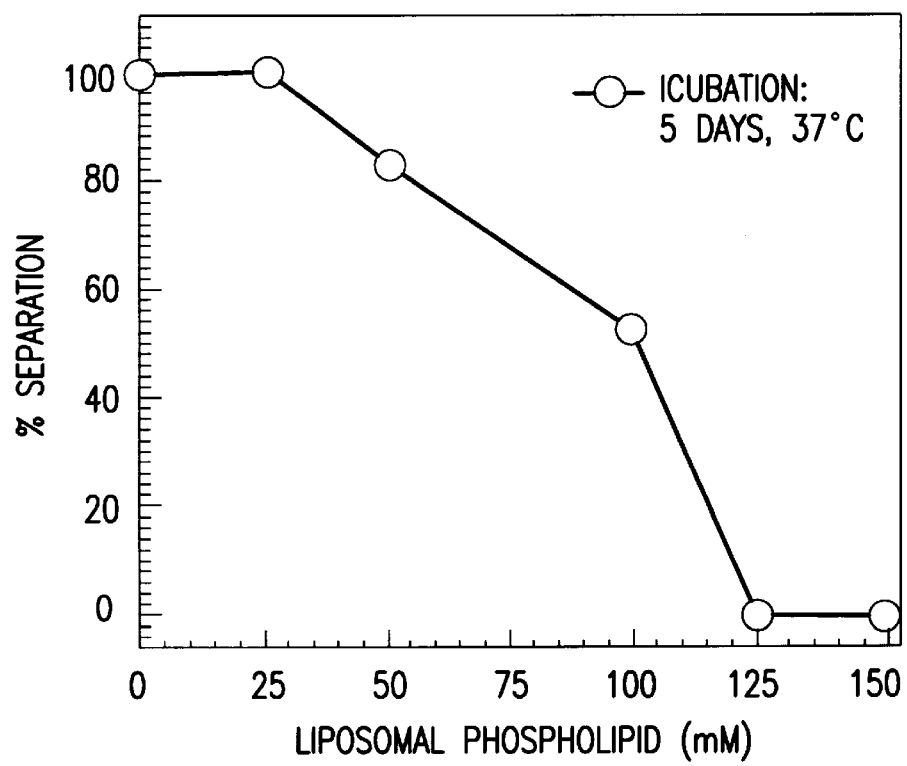
FIG. 1 is a graph showing the stabilization of oil-in-water emulsions by phospholipid-containing vesicles.

The invention compositions are stabilized oil-in-water emulsions which contain, as their sole stabilizing agent, smectic mesophase vesicles, often commonly known as liposomes. As described below, the emulsified formulations are suitable for delivery of drugs, especially vaccines, to subjects so that the pharmacokinetics of the delivery of the active ingredient or active ingredients is favorably influenced by the nature of the formulation. The emulsions of the invention are obtained by mixing, under appropriate conditions, a suspension of sm-vesicles, typically liposomes, with a suitable oil, preferably mineral oil. However, additional oils can be used as illustrated below, including vegetable oils, silicone oils and the like.

The composition used in preparing the emulsion is important in assuring an appropriate distribution of intact and disintegrated liposomes. It is believed that the presence of this distribution is thought to be essential achieving the advantageous effects of this composition. Suitable distributions can be obtained by adjusting the ratio of the oil component to the aqueous suspension, and by supplying an appropriate concentration of sm-vesicles. Typically, the sm-vesicles must be supplied to the emulsion at a level which will provide in the range of 100–150 mM phospholipid in the case of liposomes or of nonionic surfactant in the case of niosomes. Preferably the concentration of phospholipid or nonionic surfactant in the formulation is in the range of 90–140 mM, more preferably 90–120 mM, most preferably 90–110 mM. Typically, the proportion of the disintegrated liposomes will be in the range of 20–50%, more preferably 30–40%. The preferred ratios of oil to water in the compositions are in the range of 5–40% oil/water (v/v), more preferably 6–30%, still more preferably 6–20%, and most preferably on the order of about 10%.

The method of preparing the emulsion in order to effect a suitable distribution of intact and disintegrated liposomes is of great importance. Mechanical agitation, such as by vortexing, is relatively ineffective; most preferably, the formulations of the invention are prepared by methods which supply shear forces to the liposomal preparation. Thus, the emulsions of the invention are typically prepared by extrusion mixing of the oil with a suspension of the sm-vesicles. In many medical applications, this can be done at the patient's bedside by engaging two syringes, one containing oil and the other suspended sm-vesicles, through simple tubing and manipulating the plungers of the syringes so as to mix the two components thoroughly. On a larger scale, microfuidizers may be employed. The method or preparation, however, must result in the appropriate distribution of intact/disintegrated sm-vesicles and is effected through methods that provide shear forces to the sm-vesicle suspension.

The sm-vesicle suspension used to prepare the emulsion is the sole emulsifying agent used to stabilize the resulting formulation. The nature of sm-vesicles is discussed, for example, by Small, D. M., "The Physical Chemistry of Lipids, from Alkanes to Phospholipids," *Handbook of Lipid Research* (19) 4:49–50; Plenum N.Y. Smectic mesophases are defined therein as follows:

When a given molecule is heated, instead of melting directly into an isotropic liquid, it may instead pass through intermediate states called mesophases or liquid crystals, characterized by residual order in some directions by lack of order in others . . . In general, the molecules of liquid crystals are somewhat longer than they are wide and have a polar or aromatic part somewhere along the length of the molecule. The molecular shape and the polar-polar or aromatic interaction permit the molecules to align in partially ordered arrays . . . These structures characteristically occur in molecules that possess a polar group at one end. Liquid crystals with long-range order in the direction of the long axis of the molecule are called smectic, layered or lamellar liquid crystals . . . In the smectic states, the molecules may be in single or double layers, normal or tilted to the plane of the layer and with frozen or melted aliphatic change.

A common name for vesicles comprising smectic mesophases is "liposomes," especially when phospholipid is used as an amphiphile. These vesicles are formed from smectic mesophases and generally contain molecules with a hydrophobic region and a hydrophilic or polar region. Such molecules are often referred to as amphiphiles or as amphipathic molecules. In vesicles, the formation of the smectic mesophase is accomplished by including such amphiphiles. The amphiphile is commonly a phospholipid, but need not be. Other amphiphiles that may be used to prepare "niosomes," i.e., smectic mesophase vesicles which are, technically speaking, not liposomes, include molecules where polyethylene glycol, polyglycerol, sorbitan or a sugar constitute head groups—i.e., nonionic surfactants such as sorbitan monolaurate (Span 20), sorbitan monopalmitate (Span 40), sorbitan monostearate (Span 60) and sorbitan monooleate (Span 80).

While the word "liposomes" is often loosely used to include niosomes, since technically niosomes and liposomes are different in their compositions, and since it would be possible to prepare vesicles in which both a phospholipid and a nonionic surfactant serve as amphiphiles, it is preferred to use the term "smectic mesophase vesicle" or sm-vesicle to denote the vesicles useful in the compositions of the invention.

Applicants have found, unexpectedly, that a suitable concentration of sm-vesicles contained in an oil-in-water emulsion will stabilize the emulsion from "breaking" without the requirement for additional emulsifier, even though relatively low concentrations of sm-vesicles in oil-in-water emulsions already stabilized by an emulsifier effect a breakdown of the emulsion into two phases. While not intending to be bound by any theory, applicants believe that the oil-in-water emulsions of the invention containing only sm-vesicles as stabilizers experience the disintegration of a portion of the vesicles, releasing the amphiphilic components as endogenous emulsifiers. When the concentration of vesicles exceeds that required to stabilize the emulsion—i.e., prevent the emulsion from breaking—the remainder of the vesicles contained in the composition remains stable for indefinite periods.

The intact sm-vesicles residing in the emulsions of the invention can be modified to contain, e.g., encapsulate, a variety of suitable ingredients. Among these ingredients are immunogens, adjuvants, and therapeutic substances. Depending on the nature of the ingredient to be included, the ingredient may be encapsulated within the sm-vesicle or may be included within the smectic mesophase thereof Thus, the sm-vesicles may be provided with various imtinunogens such as prostate-specific antigen (PSA), malaria antigens, typhoid toxoids, tetanus toxoid, and the like. The compositions can further contain adjuvants per se such as Lipid A which further enhance the immunogenicity of the antigens. By supplying the antigen in the compositions of the invention, some of the antigen as administered will be encapsulated in liposomes and some, that originally encapsulated in liposomes that have disintegrated in order to supply an amphiphile as an emulsifier, will be present in exposed form. The availability both of encapsulated and nonencapsulated antigen has the advantage of activating both cellular and humoral immune systems. Furthermore, the presence of the oil in the emulsion behaves to stimulate cytokines which can attract antigen-presenting cells to the active ingredient in the vaccines.

The emulsions of the invention, thus, have particular advantages in pharmaceutical compositions. Again, without intending to be bound by any theory, it appears that the distribution of the active ingredient wherein a portion of the active ingredient is unencapsulated and a portion remains encapsulated in liposomes is particularly advantageous in obtaining appropriate pharmacokinetics.

Liposomes or niosomes may be employed in the present invention. For liposomes phospholipids are included and the liposomes may carry a net positive charge, a net negative charge or can be neutral. Inclusion of diacetylphosphate is a convenient method for conferring negative charge; stearylamine can be used to provide a positive charge. Preferably, the lipids are diacylglycerols wherein at least one acyl group comprises at least 12C, preferably between 14–24C. It is also preferred that at least one head group of the phospholipids—i.e., the portion of the molecule containing the phosphate group—is a phosphocholine, a phosphoethanolamine, a phosphoglycerol, a phosphoserine, or a phosphoinositol.

Stock solutions of lipids in chloroform or chloroform/methanol can be stored at about $-20°$ C. Preferably, chloroform is used as the only solvent since it is more readily evaporated than methanol.

Phospholipids may be obtained from natural sources, such as egg or soybean phosphatidylcholine, brain phosphatidic acid, brain or plant phosphatidylinositol, heart cardiolipin, or plant or bacterial phosphatidylethanolamine. However, these are preferably not used as the primary phosphatides—i.e., constituting more than 50% of the total phosphatide composition. It is preferred to use commercially available, relatively pure phospholipids.

In the present invention, liposomes may comprise lipids in any molar ratio and optionally contain cholesterol. Preferably, DMPC, DMPG and cholesterol are combined at molar ratios of about 9:1:7.5.

As used herein, the term "liposomal lipid mixture" refers to those components which make up the structural portion, i.e., the lipid bilayer, of the liposome encapsulating the substance contained in aqueous medium enclosed therein.

There are a number of methods available for making liposomes, the size depends on the method chosen. Generally, liposomes suspended in aqueous solution are spherical and have one or several concentric lipid bilayers. Each monolayer consists of a parallel array of molecules represented by the formula XY wherein X is hydrophilic and Y is hydrophobic, in aqueous solution the concentric layers are arranged such that the hydrophilic moieties remain in contact with aqueous phase and hydrophobic regions self-associate. When aqueous phases are present both inside and outside the liposome, the lipid molecules form a bilayer, known as a lamella, of the arrangement XY–YX.

Typically, liposomes are prepared by mixing the phospholipid and other components which form part of the structure of the liposome in an organic solvent, evaporating off the solvent, resuspending in aqueous solvent, and finally lyophilizing the lipid/phospholipid composition. The lyophilized composition is then reconstituted in a buffer containing the substance to be encapsulated.

In a particularly preferred method, the liposomes are prepared by mixing the liquids to be used, including lipid A, in the desired proportion in a container such as a glass pear-shaped flask having a volume ten times greater than the anticipated suspension of liposomes. Using a rotary evaporator, the solvent is removed at approximately $40°$ C. under negative pressure. The vacuum obtained from a filter pump aspirator attached to a water faucet may be used. The solvent is normally removed within about 2–5 minutes. The composition may then be dried further in a desiccator under vacuum, and is stable for about one week.

The dried lipids may be rehydrated at approximately 30 mM phospholipid in sterile, pyrogen-free water by shaking until all lipid film is off the glass. The aqueous liposomes can then be separated in aliquots, lyophilized and sealed under vacuum.

Alternatively, liposomes can be prepared according to the method of Bangham et al. *J Mol Biol*(965) 13:238–252; or as described by Gregoriadis in *Drug Carriers in Biology and Medicine*, G. Gregoriadis, Ed. (1979) pp. 287–341; or by the method of Deamer and Uster as described in *Liposomes*, M. Ostro, Ed. (1983); or by the reverse-phase evaporation method described by Szoka et al. *Proc Natl Acad Sci USA* (1978) 75:4194–4198. Depending on the choice of method, the resulting liposomes will have various abilities to entrap aqueous material and differ in their space-to-lipid ratios.

Although the description above has, for ease of presentation, focused on "liposomes," similar procedures are available to prepare niosomes wherein nonionic surfactants substitute for phospholipids. As liposomes are used in the illustrative formulations herein, this language has been used for simplicity. However, the scope of the invention extends to sm-vesicles which include both niosomes and liposomes. In any discussion employing the terminology related to "liposomes," it is intended that similar procedures can be followed to prepare or use niosomes but substituting nonionic surfactants for phospholipids.

The sm-vesicle preparations of the invention are typically rehydrated, as described above, in the presence of an active ingredient. The active ingredient will be a "therapeutically active ingredient"—i.e., a medicament or an immunogen useful in treatment of humans and other animals. Thus, the emulsions of the invention are pharmaceutical or veterinary formulations. The formulations may, of course, contain more than one active ingredient.

The ultimate formulations of the present invention are preferably used as vaccines, where the active ingredient is an immunogen. The vaccines of the invention may prevent, treat, ameliorate, or otherwise affect a condition in a manner that is desirable to the host harboring the condition. Thus, the vaccines may be used to prevent infection or to ameliorate its symptoms if nevertheless culminated, to mount an immune response against an undesired tissue, such as tumor, in which case the vaccine may be used either to prevent tumor formation or to cause regression or slow tumor growth. In general, the word "vaccine" encompasses any immunologic composition which elicits a desired response from the immune system. That immune response may modulate an existing condition as well as prevent the onset of the undesired condition or inhibit its progress.

In the vaccines of the invention, the immunogen is the desired antigen representing the organism or tissue against which immunity is desired. Suitable antigens include, for example, viral-derived peptides, bacterial-derived peptides, tumor markers and the like. Antiviral vaccines against rotavirus, influenza virus, herpes simplex virus, chicken pox, and the like can thus be prepared. Similarly, vaccines against infection by Staphylococcus, Tetanus, Diphtheria, or other bacterial diseases are formulated in this manner as well. Suitable antigens also may comprise tumor-associated markers, as well as prostate-specific antigen (PSA) for immunization with respect to prostate cancer or KSA as an additional tumor associated antigen.

The ultimate formulations can also include an adjuvant. The adjuvant is typically, although not necessarily, supplied in the context of the liposomal or niosomal portion of the formulation and can be included along with the amphifiles in the preparation of the sm-vesicle suspension. Suitable adjuvants include Lipid A, various alums, surface-active agents such as ISCOMS, sapanin and Vitamin E, polyanions such as dextran, or doublestranded nucleotides, bacterial products such as muramyl dipeptides and tripeptides, trehalose dimycolate, Bordetella pertussis, Bacillus Calmette Guerin, various cytokines such as interleukins 1 and 2 and interferons α and γ, peptides such as 3-threonyl-L-lysyl-L-prolyl-L-arginine, polyacrylates and N-acetyl glucosamine-3-yl-acetyl-L-alanyl-D-isoglutamine.

The antigens may be coupled to carriers to enhance immunogenicity, such carriers include VP6 from rotavirus, bacterial toxoids, such as Diphtheria toxoid, fatty acids, bentonite, cholera toxin D subunit, and keyhole limpid hemocyanine. The epitopes may also be generated in situ using vectors such as vaccinia virus, adenovirus, and attenuated Salmonella.

The ultimate formulations of the invention can also behave as drug delivery systems with the release of drug from the sm-vesicles governed by the ratio of oil to vesicles in the composition. Thus, the active ingredient included in the aqueous liposomal suspension used to prepare the final formulated emulsion may include any suitable drug, such as antibiotics, antiinflammatories, blockers for various receptors, vitamins, analgesics, and other small-molecule drugs. In addition, peptide or protein based drugs can also be administered in this manner. Such active ingredients as erythropoietin, tPA, insulin, growth hormone, and various colony stimulating factors, among others, can be administered in this manner.

Typically, the compositions are administered by injection, intramuscular, intravenous, subcutaneous, intraperitoneal and the like. However, in addition, these compositions may be administered topically, by inhalation, or by suppository. Topical administration on the skin is especially advantageous in some indications.

The dosage level will depend on the nature of the active ingredient, the condition of the subject, the judgment of the practitioner, and a variety of other factors that are dependent on the specific circumstances of the subject. The formulations of the invention are useful in a broad range of pharmaceutical applications, with dosage levels dictated by the conditions at hand.

These examples are intended to illustrate but not to limit the invention.

Preparation A

Preparation of Liposomes

Liposomes are prepared according to the procedure of Alving, C. R. et al. in *Liposome Technology: Interactions of Liposomes with the Biological Milieu* (1993) *III*: CRC Press, Boca Raton, Fla., pp. 317–343. Additional descriptions are found in Verma, J. N. et al. *Infect Immun* (1992) 60:2438–2444, and in Richards, R. L. et al. *Infect Immun* (1988) 56:682–686. Table 1 below shows abbreviations used for the components that may be employed.

TABLE 1

| Abbrev. | Name | No. Carbons in each acyl | No. π-bonds in each acyl |
|---|---|---|---|
| DLPC | dilauroyl phosphatidyl-choline | 12 | 0 |
| DMPC | dimyristoyl phosphatidyl-choline | 14 | 0 |
| DPPC | dipalitoyl phosphatidyl-choline | 16 | 0 |
| DSPC | distearoyl phosphatidyl-choline | 18 | 0 |
| DOPC | dioleoyl phosphatidyl-choline | 18 | 1 |
| DLnPC | dilinoleoyl phosphatidyl-choline | 18 | 2 |
| DMPG | dimyristoyl phosphatidyl-glycerol | 14 | 0 |
| CHOL | cholesterol | | |
| LA | Lipid A | | |

In a typical preparation, multilamellar liposomes are made from a mixture of DMPC:DMPG:CHOL:LA in a molar ratio of 9:1:7.5:0.011. The lipid A is included as an adjuvant. The lipid mixture is rotary evaporated to a dry thin film at approximately 40° C. in vacuo from a chloroform solution in a pear-shaped flask. To ensure complete removal of the organic solvent, the flask is then dried under very low vacuum (about 0.05 mm Hg) overnight in a desiccator at room temperature. After drying, the lipids are carefully swollen in deionized, sterile pyrogen-free water by vortexing. The resulting suspension is frozen at −55° C., lyophilized at −20° C. overnight and 0° C.–10° C. the following day using the Virtis Unitop 800SL Freeze Mobile (the Virtis Company, Gardener, N.Y.).

The lyophilized lipids are then reconstituted in the presence of the substance to be encapsulated to obtain multilamellar liposomes containing this substance. A suitable reconstituting buffer is phosphate-buffered saline (PBS) or Tris-glycine/NaCl. The liposomal phospholipid concentration in the reconstituting buffer is 10–200 mM.

Unencapsulated substance may be removed by washing the liposomes three times with 0.15 M NaCl at 27000×g for 10 minutes at 10° C. The resulting liposomes are suspended either in 0.15 M NaCl or an appropriate isotonic buffer to reach a final phospholipid concentration of 10–200 mM. Alternatively, the wash step may be omitted, leaving both unencapsulated and encapsulated antigen in the preparation. However, inclusion of a wash step is greatly preferred.

EXAMPLE 1

Effect of Liposomes on Emulsion Stability

An oil-in-water emulsion was prepared from mineral oil using the method of Rudbach, J. A. et al., *Adjuvants: Theory* and *Practical Applications* (Stewart-Tull, Ed., John Wiley & Sons, New York, in press) or Schneerson, R. et al. *J Immunol* (1991) 147:2136. Various amounts of a liposome preparation composed of DMPC:DMPG:CHOL:LA (9:1:7.5:0.11) were added to the emulsified o/w composition which contained no other stabilizer. FIG. 1 shows the stabilizing effects of various amounts of the liposome composition. Stability (or instability) is shown as percent separation after five days at 37° C. as a function of the concentration of liposomal phospholipids. As shown, when the liposomal phospholipid concentration reaches 100 mM or more, substantial stabilization of the preparation is obtained. The emulsion appears essentially completely stable after this time at this temperature when the liposomal phospholipid concentration is 125 mM or greater.

These findings are in contrast to the effect of liposomes on a "stabilized" water-in-oil (w/o) emulsion. Incomplete Freund's Adjuvant, stabilized with Arlacel A, was supplemented with 0%, 5%, 20% and 50% liposomes and incubated at 4° C. for 15 days. The percent separation at these concentrations was 1.3%, 5.71%, 20% and 40%, respectively. Thus, the result for o/w compositions upon addition of liposomes is markedly different from the water-in-oil counterparts.

Figure 2A:
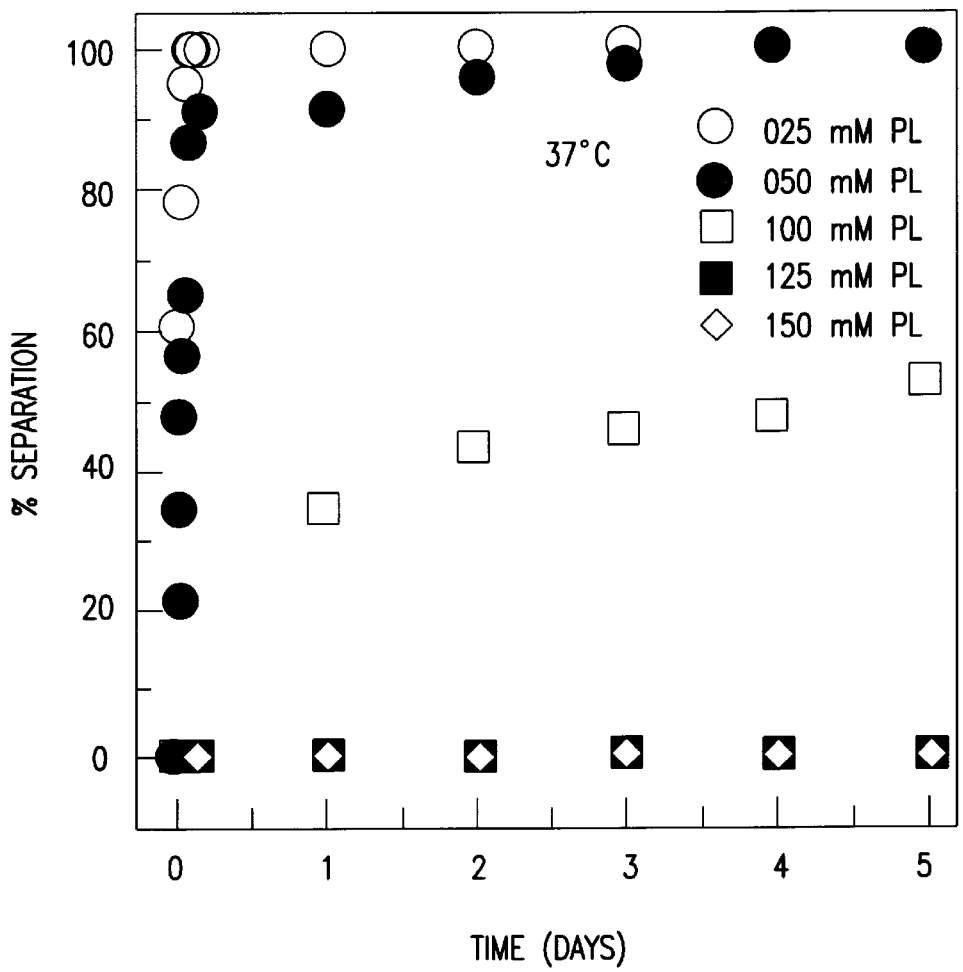
FIGS. 2a and 2b are graphs showing the stabilization of oil-in-water emulsions by liposomes when these emulsions are prepared by a syringe-extrusion procedure or a vortex-mixing procedure.

The kinetics of stabilization of liposomes on mineral oil-in-water emulsions prepared by a syringe extrusion procedure was tested at various concentrations of liposomes prepared as described above. FIG. 2a shows the results obtained when the emulsions were incubated at various concentrations of liposomes at 37° C. As shown, liposomal concentrations providing 125 mM phospholipid or more gave o/w emulsions that were stable to the level of detection for at least five days. The addition of liposomes corresponding to 100 mM phospholipid resulted in stabilizing the emulsion at a level of 40% separation which was reached after approximately one day. However, smaller amounts of liposomes failed to stabilize the emulsion, which showed 100% separation in less than a day.

Figure 2B:
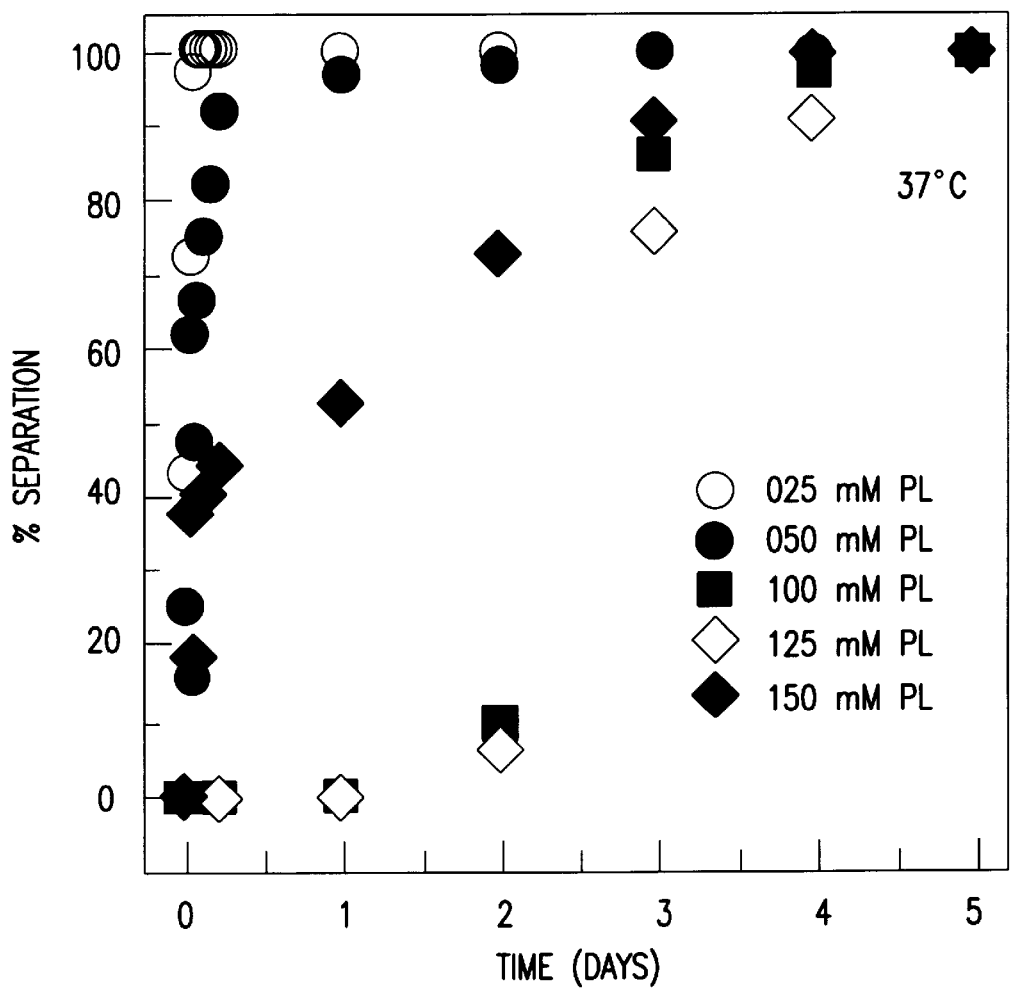
Figure 3A:
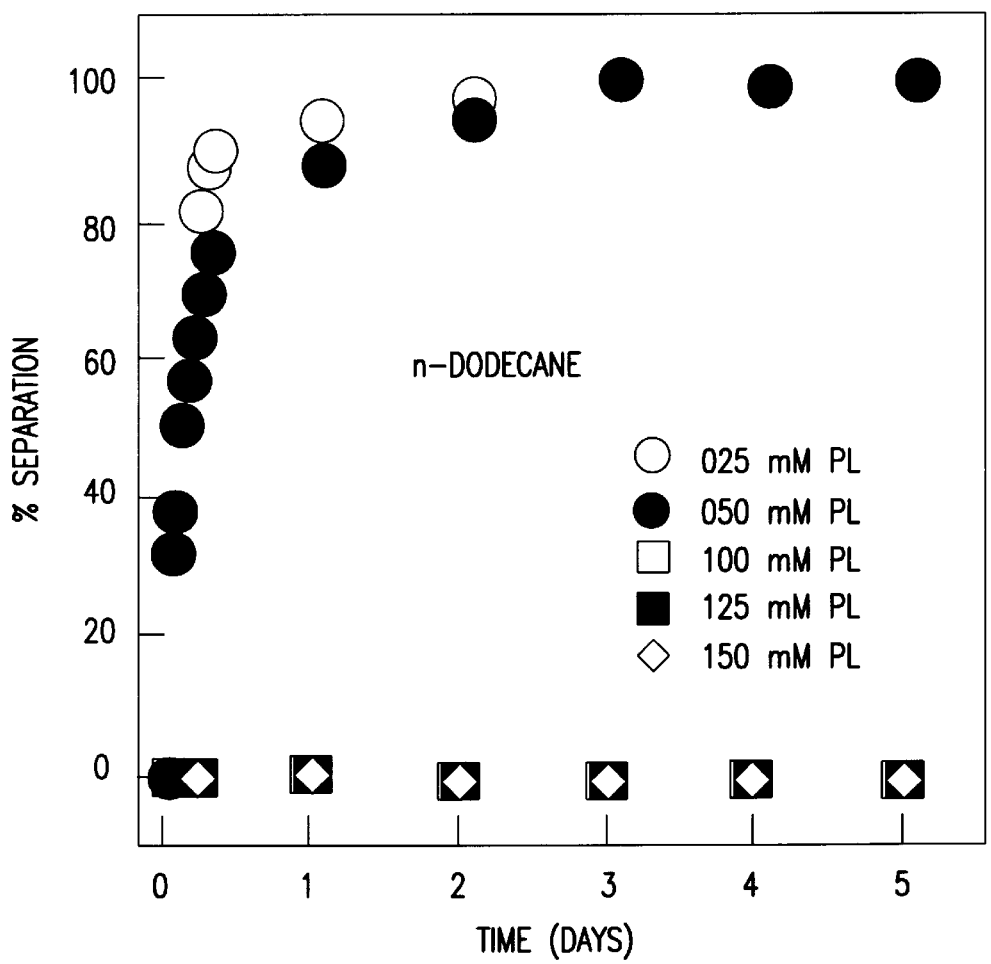
FIG. 3a–f is a series of graphs showing stabilization of various oil-in-water emulsions by sin-vesicles (see below) at 37° C.
Figure 3B:
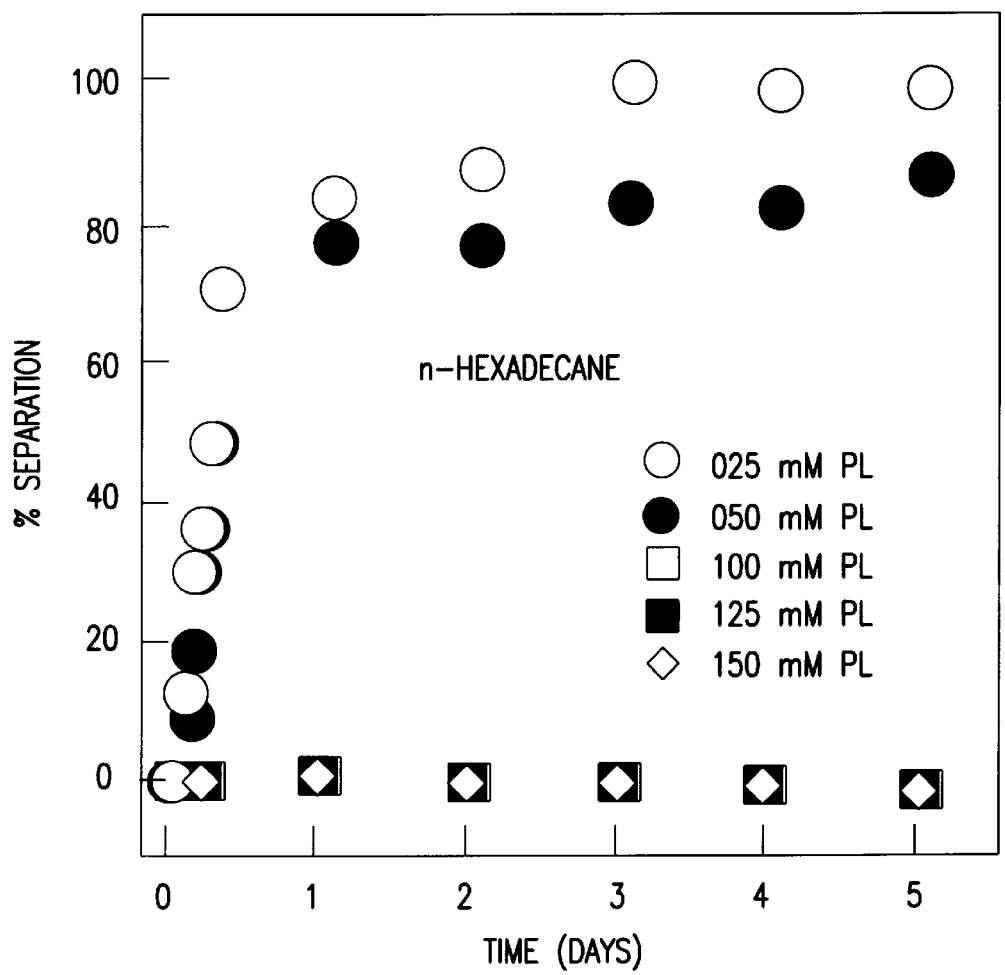
Figure 3C:
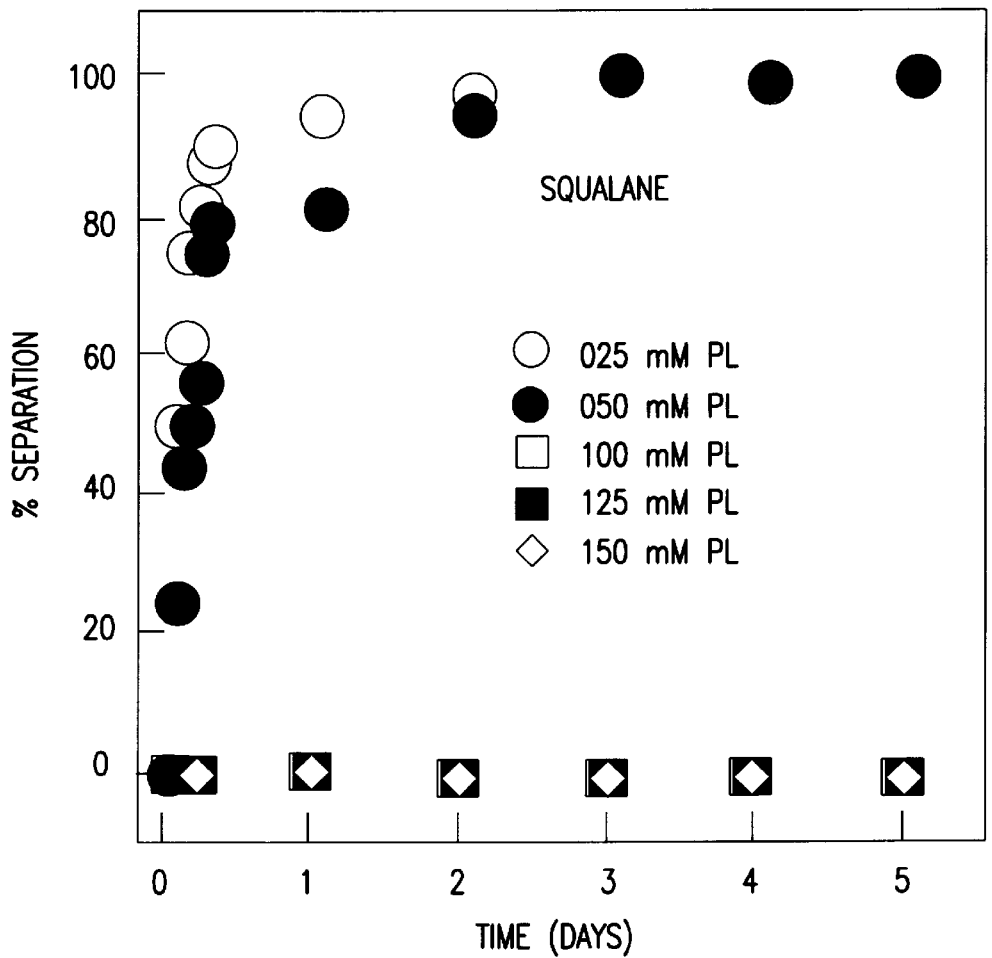
Figure 3D:
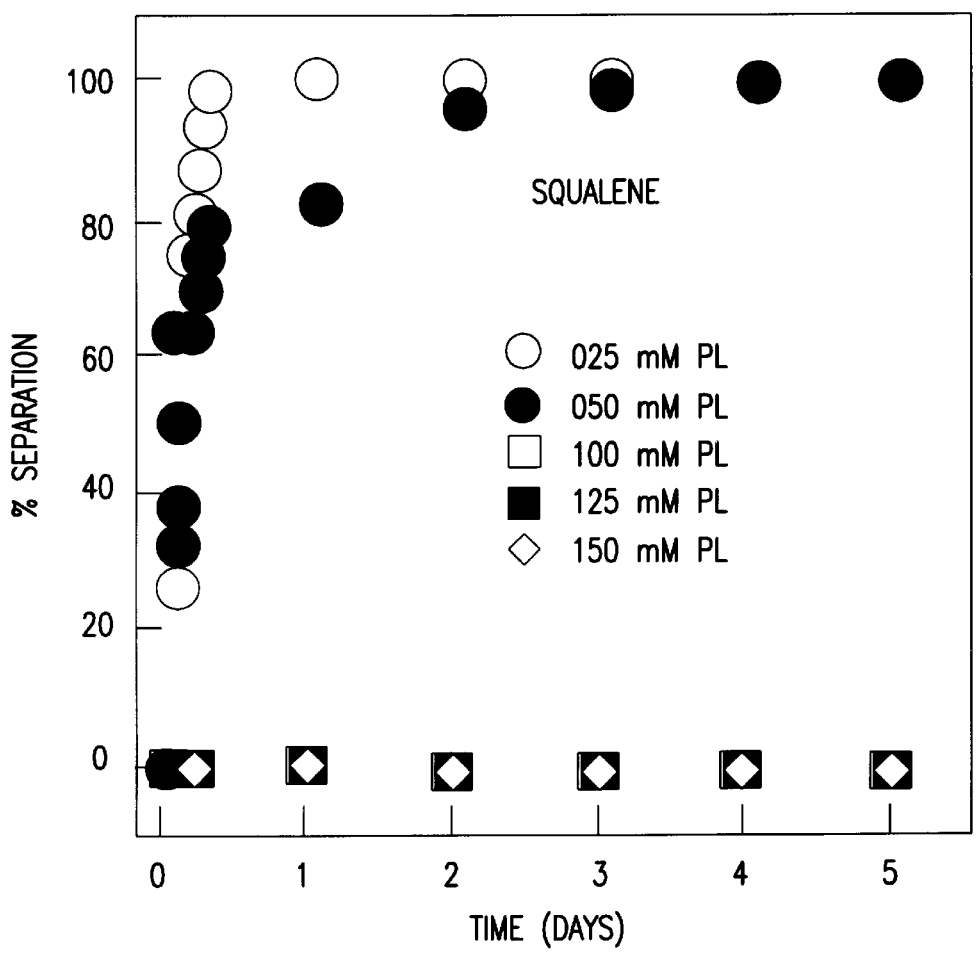
Figure 3E:
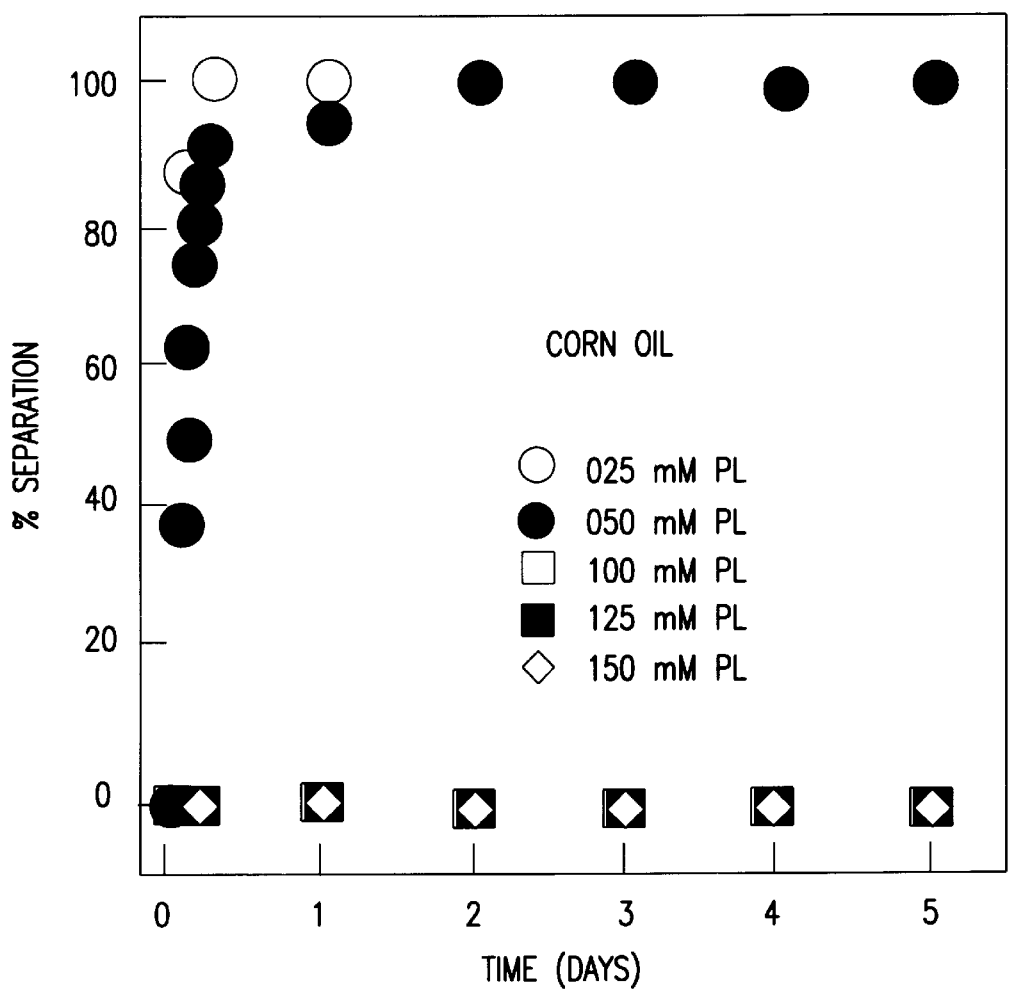
Figure 3F:
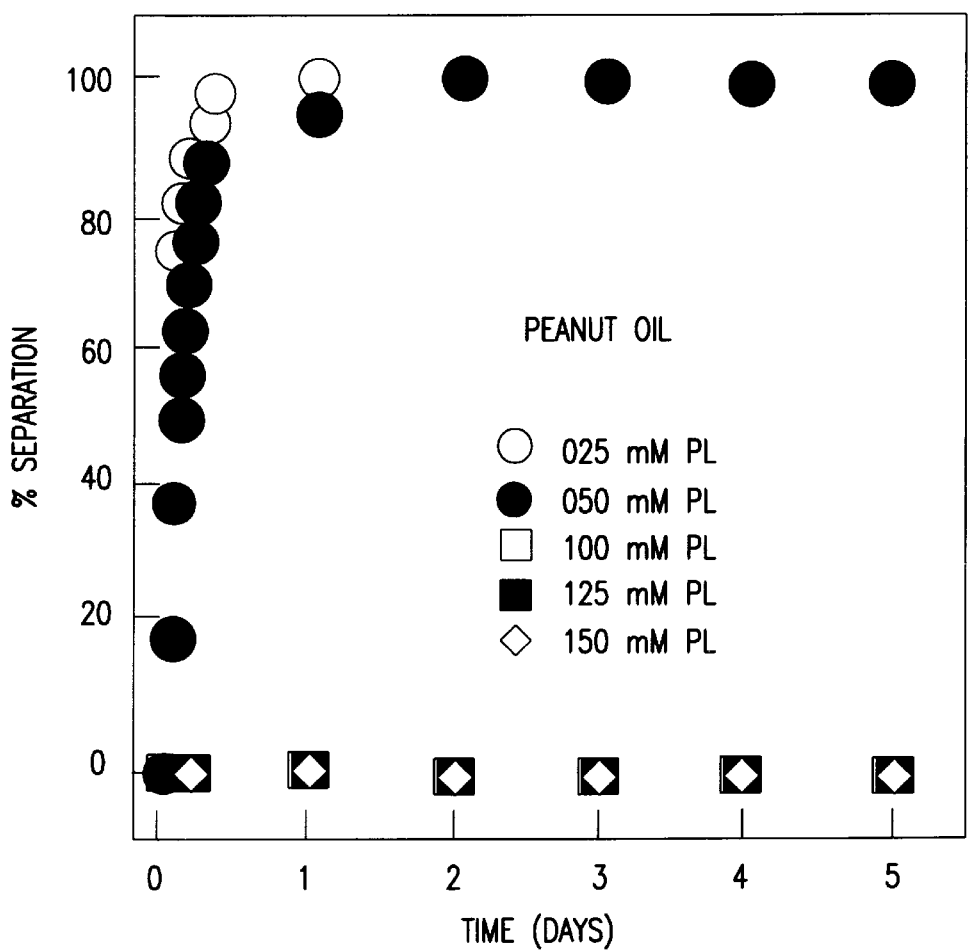

Results obtained when the oil-in-water emulsions were prepared by a vortex mixing procedure differed from those obtained from syringe mixing. This is shown in FIG. 2b. While again, 125 mM phospholipids provided by liposomes showed a stabilizing effect, this was dramatically less than for the emulsions prepared by the syringe extrusion procedure, and for far shorter times. The results obtained with 100 mM phospholipid were similar to those obtained with 125 mM phospholipid. Interestingly, with higher amounts, at 150 mM phospholipid, the emulsion appeared less stable and began to separate almost immediately. At amounts lower than 100 mM phospholipid, separation began immediately and was almost complete before the end of one day, as was the case with the syringe extrusion procedure.

EXAMPLE 2

Effect of the Nature of the Oil Components

The experiments set forth in Example 1 were repeated using, various oils in the o/w emulsion, including N-dodecane, N-hexadecane, squalane, squalene, corn oil, and peanut oil. The results are shown in FIG. 3. In all cases, again, the addition of liposomes sufficient to provide 125 mM phospholipid resulted in emulsions with no detectable separation after five days. In these experiments liposomes sufficient to provide 100 mM phospholipid also provided this result. However, lower phospholipid concentrations failed to stabilize the emulsions which separated in all cases over a period of one day or less.

EXAMPLE 3

Structural Integrity of Liposomes in Emulsions

To test for structural integrity of the liposomes themselves in the context of the emulsions, liposomes were prepared as in Example 1 encapsulating glucose. The emulsion was prepared by mixing the liposome preparation with mineral oil wherein the mineral oil was used at a concentration of 10.2% (v/v) or 42.5% (v/v). The emulsions were prepared either by vortex mixing or by syringe extrusion mixing. Various concentrations of liposomes were included in the aqueous phase and the percent trapped glucose released after 15 minutes at 37° C. was followed by centrifuging the samples at 27000×g for 10 minutes and assaying the supernatant for free glucose. The results are shown in FIGS. 4a and 4b.

Figure 4A:
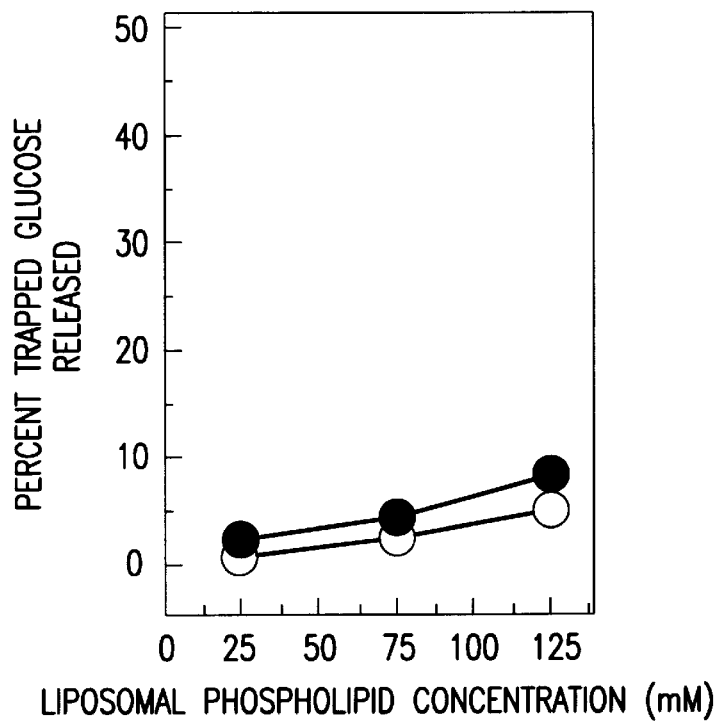
FIG. 4a–b shows the release of glucose marker from various oil-in-water emulsions containing sm-vesicles as stabilizers 15 minutes after forming the emulsion.

As shown in FIG. 4a, at phospholipid concentrations from 25–125 mM and at both ratios of oil-to-aqueous component, glucose remained entrapped in the liposome. Even at 125 mM phospholipid, less than 10% of the entrapped glucose was released. (In FIGS. 4a and 4b, the solid circles represent 42.5% oil and the open circles represent 10.2% oil.)

Figure 4B:
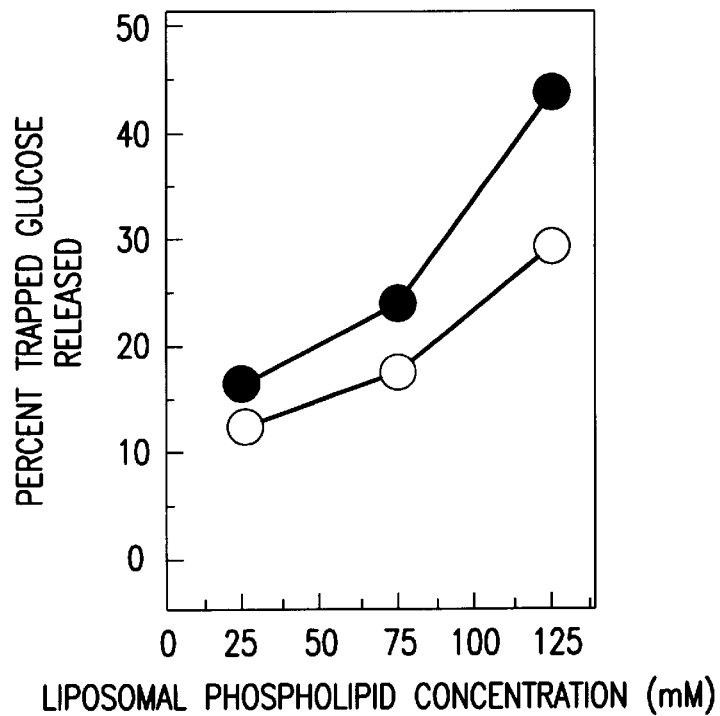

As shown in FIG. 4b, when syringe extrusion was used to prepare the emulsion, glucose was immediately released into the supernatant. For the 10.2% oil compositions, at 125 mM phospholipid, 30% of the entrapped glucose was released. At higher oil concentrations, i.e., 42.5%, and 125 mM phospholipid, almost 50% of the entrapped glucose was released after the short incubation period.

While not intending to be bound by any theory, applicants believe that the stabilization of the emulsion is attributable to an appropriate level of disintegration of the liposomes providing free phospholipid to entrap the oil particles suspended in the aqueous medium. The appropriate level of disintegration is apparently provided by shear forces obtainable on extrusion mixing, and does not occur when the emulsion is prepared by direct mechanical agitation in the vortexing procedure. As shown in FIGS. 2b and 4a, vortex mixing provides emulsions which contain intact liposomes but not greatly enhanced stability while, as shown in FIGS. 2a and 4b, extrusion mixing provides emulsions wherein the liposomes partially disintegrate but stability is imparted to the emulsion.

EXAMPLE 4

Efficacy of Vaccines Including Liposomes and O/W Emulsions

Figure 5A:
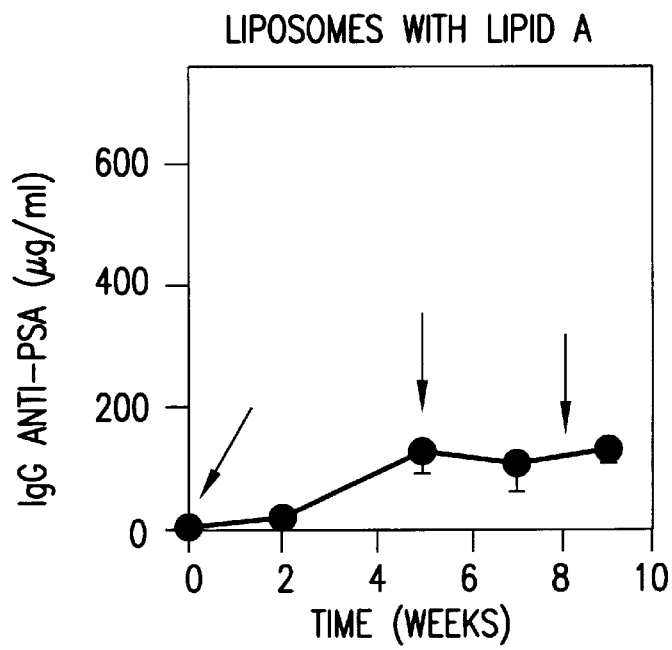
FIG. 5 is a series of graphs showing antibody responses obtained to prostate-specific antigen (PSA) contained in sm-vesicles emulsified with oil-in-water emulsions.
Figure 5B:
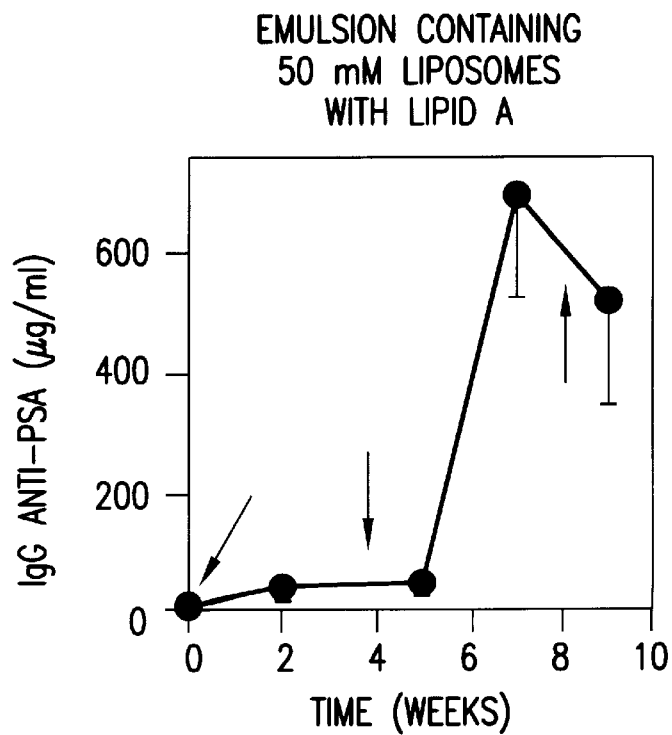
Figure 5C:
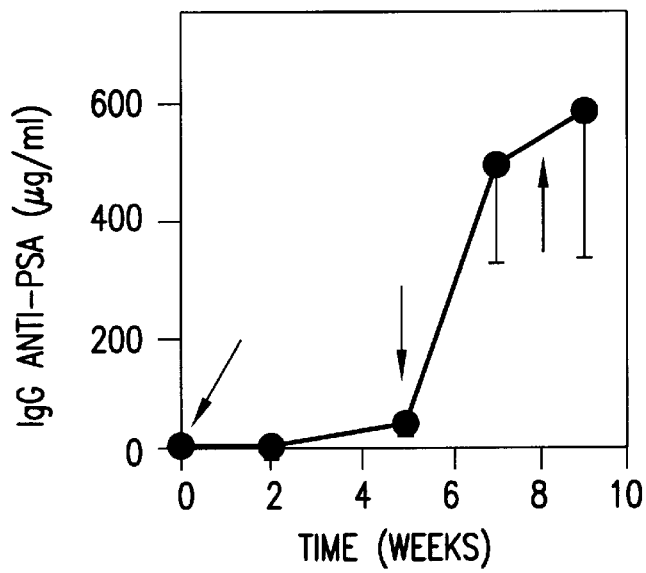
Figure 5D:
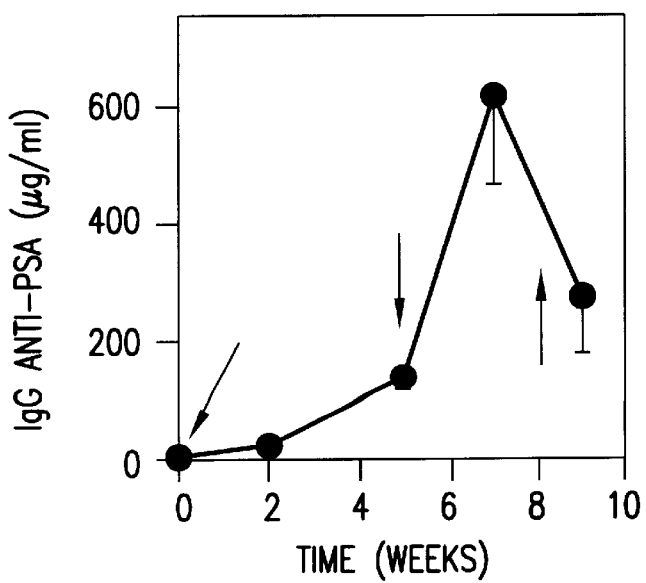

The ability of various formulations containing 10 μg of prostate-specific antigen (PSA) and 25 μg lipid A to raise antibodies in murine subjects was evaluated. The mice were injected with this quantity of PSA formulated in various compositions and the production of antibodies monitored over time. As shown in FIG. 5a, when liposomes prepared in Example 1 (including lipid A) was used as a carrier, the level of IgG anti-PSA antibodies increased gradually over four weeks to obtain a final concentration of approximately 125 μg/ml. For an emulsion prepared using the syringe extrusion method containing 50 mM phospholipid in the form of liposomes, the antibody titer did not rise until after about five weeks when a level of 800 μg/ml was obtained, this titer declined after 6 weeks (FIG. 5b). When 100 mM phospholipid as liposomes were included in the emulsion, the antibody titer did not increase until after five weeks and a final titer of about 600 μg/ml was obtained (FIG. 6c). When liposomes to provide 150 mM of phospholipid were included in the emulsion, the titers again did not begin to increase until after approximately four weeks and a final titer of 600 μg/ml was achieved after seven weeks which then declined to 300 μg/ml after nine weeks (FIG. 6d). This emulsion was thick and probably not ideal for therapeutic use.

EXAMPLE 5

Effect of Formulation on Lymphocyte Proliferation

The inclusion of liposomes in an emulsion also enhanced the stimulation of a cellular immune response in mice.

Figure 6A:
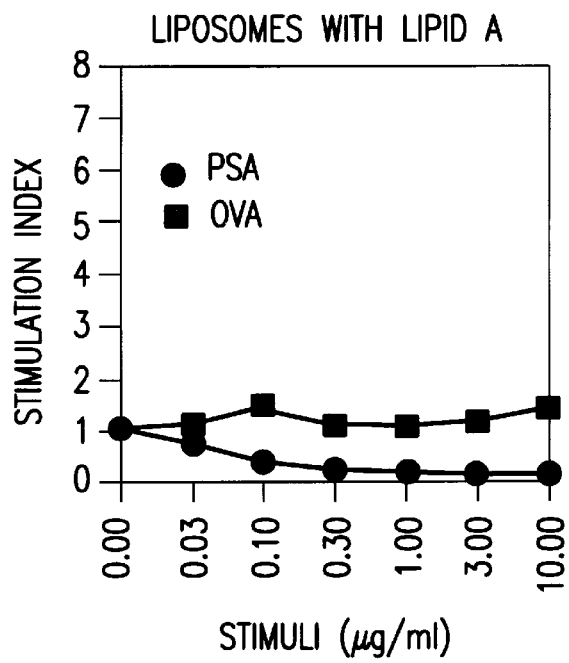
FIGS. 6a and 6b show skin test reactivity responses in mice to PSA contained in sm-vesicles in unemulsified compositions and compositions emulsified as oil-in-water emulsions.
Figure 6B:
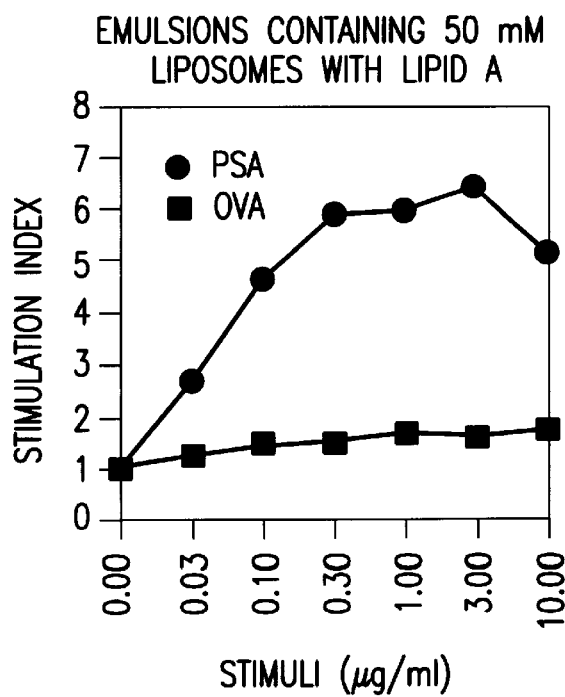

Liposomes prepared as set forth in Example 1 encapsulating 10 μg of PSA and 25 μg lipid A were injected. Spleen cells were harvested at week 13, following four immunizations with the lipsomal vaccine. Cellular responses tested after 5 days at various levels of stimulation by PSA were assessed using incorporation of tritiated thymidine as a measure of response. Neither PSA nor ovalbumin used as a control, was able to stimulate an immune response (FIG. 6a). However, when the dose of 10 μg of PSA was administered in the form of an emulsion containing liposomes encapsulating the PSA at a level to provide 50 mM phospholipid, a significant T cell response to PSA was obtained as shown in FIG. 6b while the response to the control antigen, ovalbumin, remained negative.

EXAMPLE 6

Use of Emulsified Liposome Containing Compositions in Patients

The effect of administering PSA to patients in compositions in which the PSA is encapsulated in liposomes was compared to the results when the liposomal formulation was emulsified with mineral oil.

The liposomal formulation was prepared essentially as set forth in Example 1 so as to contain about 90 μg of PSA per 0.9 ml of liposome suspension. Approximately 100 μg PSA with 200 μg lipid A were formulated in 1 ml of liposomes. In detail, liposomes were prepared using DMPC:DMPG:cholesterol at molar ratios of 9:1:7.5 and lipid A was added to obtain a final concentration of 200 μg/ml. The lipid mixture was added to water and vortexed and then lyophilized. To the lyophilized preparation, sufficient PSA was added in buffer (20 mM tris-glycine, 150 mM NaCl and 0.02% Tween 80 pH 7.4) to provide the desired concentration. PSA, 0.4 μg/ml was added to the lipophilized liposomes so that the final phospholipid concentration was 200 mM phosphate. Preliminary experiments were done to determine the percent encapsulation of PSA under these conditions. The amount of PSA to be added was determined by the desired final concentration of 100 μg/ml and the percent encapsulation which was found to be 50%. The mixture was vortexed to encapsulate the PSA and the liposomes were washed and again suspended. The suspension was used directly as a vaccine or used to prepare the emulsion.

For preparation of the emulsion, 0.9 ml of the liposome suspension was thoroughly mixed with 0.1 ml mineral oil using the syringe extrusion method. Briefly, the mineral oil and suspension were placed in separate syringes which were connected via tubing. The liquids were pulsed back and forth until an adequate suspension was obtained. The suspension was immediately used as a vaccine.

The liposome suspension was administered intramuscularly to 6 patients who had been diagnosed with tumors of prostate origin. The patients had been treated previously using various standard antitumor therapies. The particulars of these patients are shown in FIG. 7. One patient (#002) had disease progression and was removed from study before completion of the immunologic testing. He was replaced by another patient so that there would be a total of five (5) patients evaluable for immune response. The vaccine was administered by the intramuscular route on study days 0, 30, and 60. Skin test responses to PSA were measured before immunization and on study day 75. Lymphocyte proliferative and antibody responses to PSA were measured before and two weeks after each vaccination. The liposomal vaccine was administered over the period indicated in the column headed "Vaccine."

Another group of patients with prostate cancer was treated with the emulsion described above. These 5 patients also had undergone previous treatment for prostate-derived tumors. The particulars of these patients are shown in FIG. 8. The vaccine was administered over the periods indicated.

The liposomal vaccine was vialed at 1.1 ml containing 77 μg PSA and 200 μg lipid A per ml and stored at 4° C. Immediately before use, 0.1 ml of sterile, pyrogen-free light mineral oil was added and the product emulsified by passage from two glass syringes connected by plastic tubing. Each dose of the resultant emulsion consisted of approximately 70 μg of PSA with 183 μg lipid A in a 1.1 ml liposomal oil-in-water emulsion. The emulsion was given according to the same schedule used for the unemulsified vaccine: it was administered by the intramuscular route on study days 0, 30, and 60. Immunologic testing was done immediately before each vaccination and on study day 90.

The patients in each group were assessed using measured designed to determine humoral immune response as well as measures of cellular immune response. The various results obtained from these two groups are shown in FIGS. 9a,b, 10a,b and 11a,b and discussed below.

The clinical outcome in the patients is summarized in FIGS. 7 and 8. In the trial with the unemulsified vaccine, 2 of the 6 patients experienced disease stabilization at study day 90 and in one of these patients (#001, AW) the stabilization has been durable and exists to the present. Four of the 6 patients in this trial have died of their disease. Four of the 5 patients treated with the emulsified form of the vaccine had disease stabilization at study day 90 and the $5^{th}$ patient (#402, ET) had a clinical response characterized by an improved bone scan and a correlated fall in his alkaline phosphatase from 1200 to 300, along with a rise in PSA.

Figure 9A:
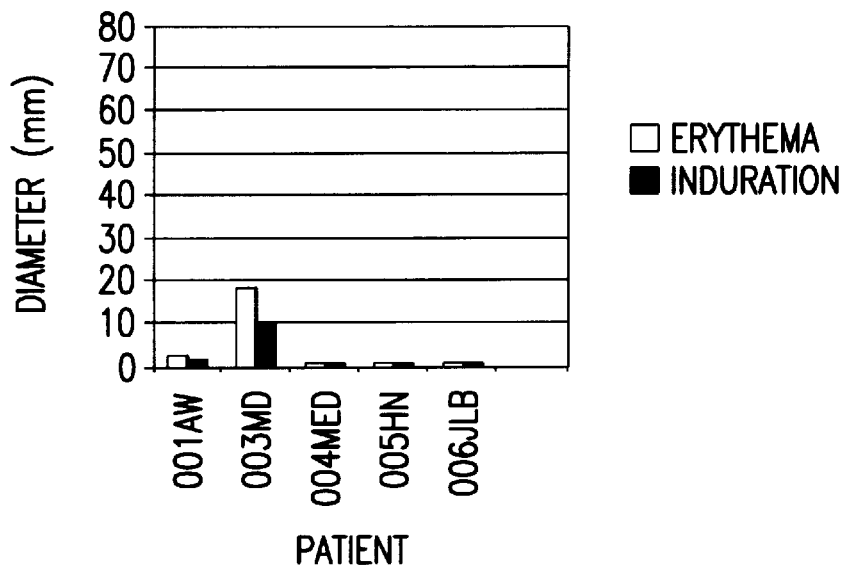
FIGS. 9a and 9b show the effect of the vaccine on skin reactivity to PSA for patients in FIGS. 7 and 8, respectively.
Figure 9B:
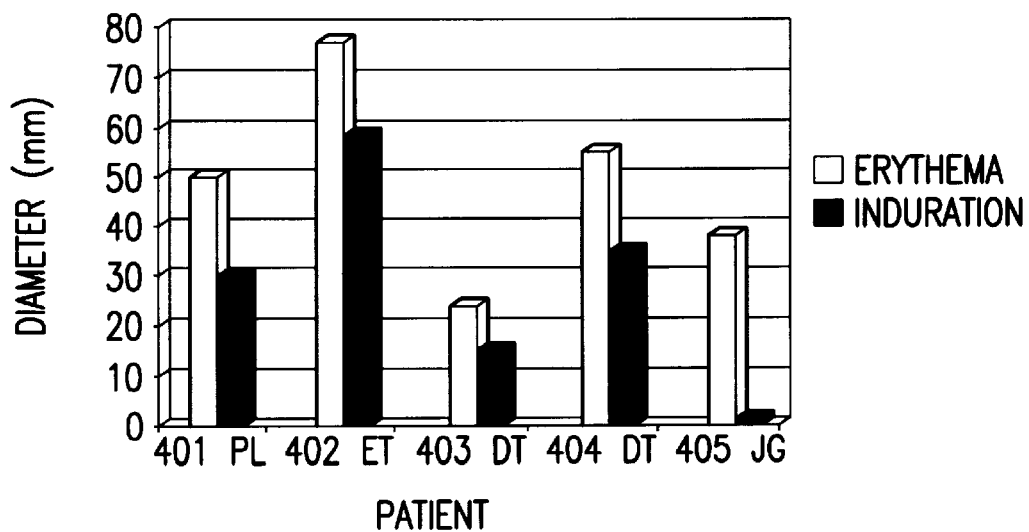

As shown in FIGS. 9a and 9b, an immune response as measured by erythema and induration was markedly stronger in patients administered the emulsion. In the group administered the liposomal formulation, only one patient (#003) showed a slight response of both erythema and induration. In the group administered the emulsion, all of the subjects gave significant responses according to both measures, with the exception of the only mild induration exhibited by patient #405.

Figure 10A:
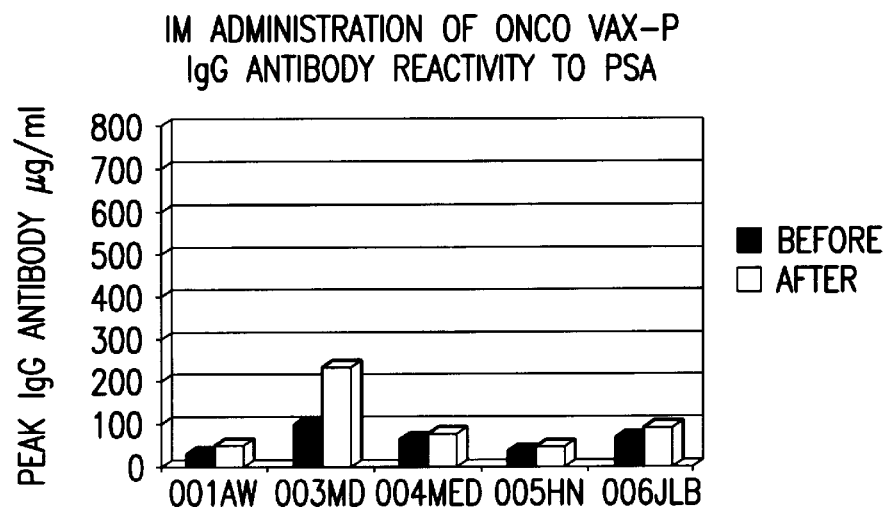
FIG. 10a and 10b show the effects of vaccine administration on anti-PSA antibody titers in the patients described in FIGS. 7 and 8, respectively.
Figure 10B:
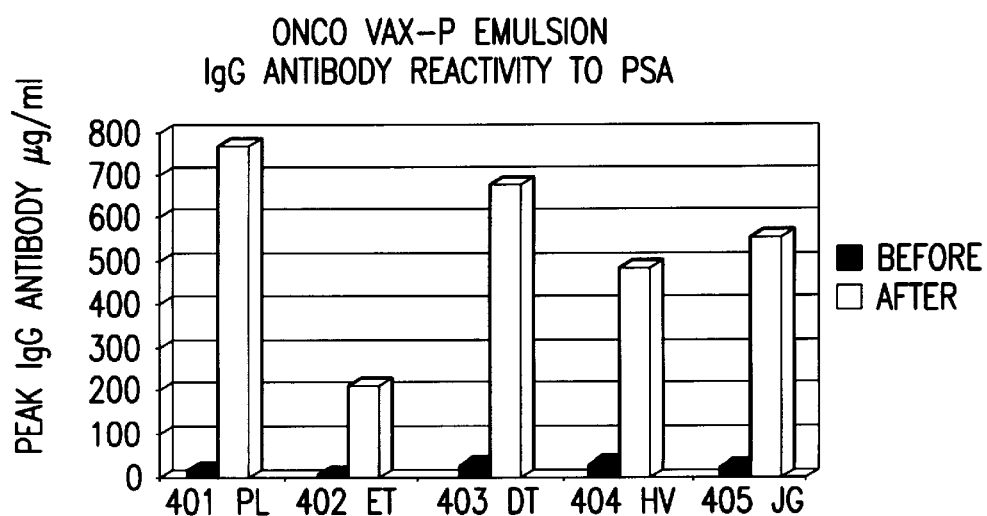

When the humoral response was measured by determining the titers of anti-PSA IgG antibodies, the patients administered the liposomal formulation showed little, if any, increase in antibodies to this antigen. See FIGS. 10a and 10b. Again, patient #003 did show a measurable response. However, all of the patients administered the emulsion showed strong antibody responses to PSA.

Figure 11A:
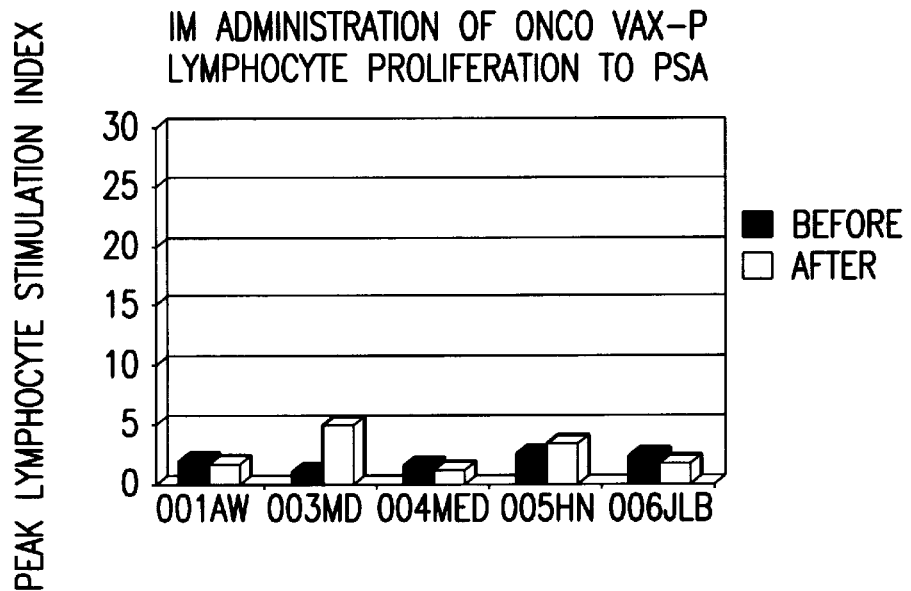
FIGS. 11a and 11b show the effects of administering nonemulsified and emulsified PSA vaccines on lymphocyte proliferation in response to PSA shown by patients described in FIGS. 7 and 8, respectively.
Figure 11B:
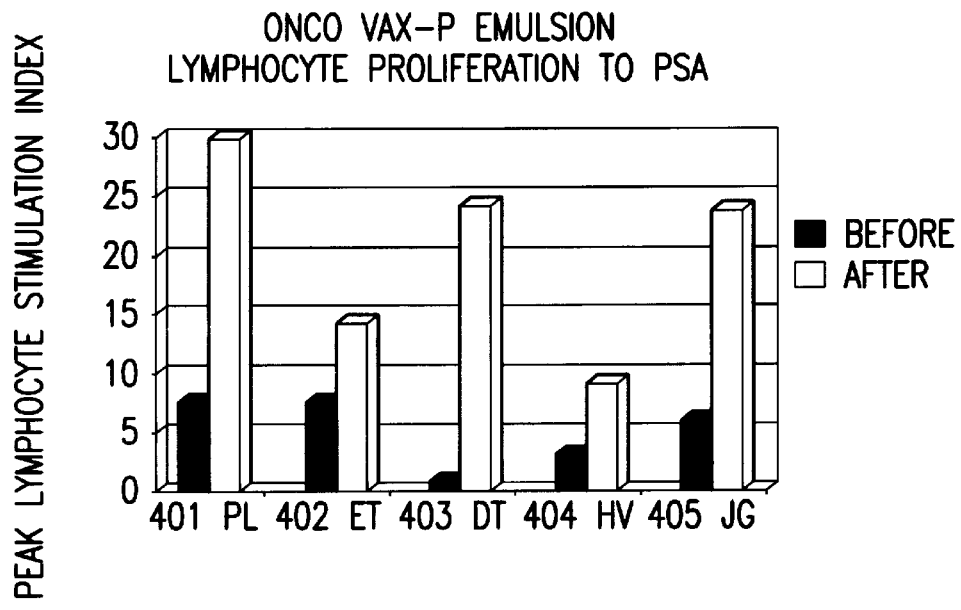

Finally, lymphocyte proliferation was measured as a means to detect a cellular immune response. None of the patients in the group administered the liposomal formulation exhibited a measurable cellular response, again with the exception of modest response shown by patient #003. See FIGS. 11a and 11b. All of the individuals in the group administered the emulsion showed strong cellular responses, as measured by lymphocyte proliferation. Thus, the emulsion composition containing liposomes functions as an effective immunogenic delivery system.

EXAMPLE 7

Parameters Affecting Emulsion Stability

The range of concentrations of liposomes and of oils in the emulsions of the invention and their on stability was studied. Table 2 shows the results of these studies where the percent separation at 37° C. after 5 minutes was determined and the period of time during which no separation could be measured was tabulated.

TABLE 2

Composition of Dispersions and Stability of Emulsions

| Mineral Oil % (v/v) | Liposomal Phospholipid in Total Emulsion (mM) | % by weight of Amphiphile in the total Emulsion | % by weight of Oil relative to weight of Amphiphile | Stability | % Separation at 37° C. |
|---|---|---|---|---|---|
| 2.65 | 25 | 4.2 | 92 | <5 min | 17.5 |
| | 50 | 8.4 | 46 | <5 min | 10.0 |
| | 75 | 12.3 | 31 | <5 min | 5.0 |
| | 100 | 16.2 | 23 | <2 hr | 10.0 |
| | 125 | 19.9 | 18 | >1 wk | 0 |
| | 150 | 24.6 | 15 | >1 wk | 0 |
| 10.6 | 25 | 4.2 | 371 | <5 min | 15.0 |
| | 50 | 8.4 | 184 | <5 min | 10.0 |
| | 75 | 12.3 | 123 | <1 hr | 5.0 |
| | 100 | 16.2 | 93 | <24 hr | 2.5 |
| | 125 | 19.9 | 74 | >1 wk | 0 |
| | 150 | 24.6 | 62 | >1 wk | 0 |
| 21.2 | 25 | 4.2 | 734 | <5 min | 10.0 |
| | 50 | 8.4 | 367 | <5 min | 7.5 |
| | 75 | 12.3 | 246 | <4 hr | 15.0 |
| | 100 | 16.2 | 186 | <72 hr | 4.5 |
| | 125 | 19.9 | 147 | >4 wk | 0 |
| | 150 | 24.6 | 123 | >4 wk | 0 |
| 42.5 | 25 | 4.2 | 1469–1488 | <5 min | 7.5 |
| | 50 | 8.4 | 734–739 | <5 min | 5.0 |
| | 75 | 12.3 | 492 | <6 hr | 20.0 |
| | 100 | 16.2 | 371 | >4 wk | 0 |
| | 125 | 19.9 | 295 | >4 wk | 0 |
| | 150 | 24.6 | 246 | >4 mo | 0 |

Figure 12:
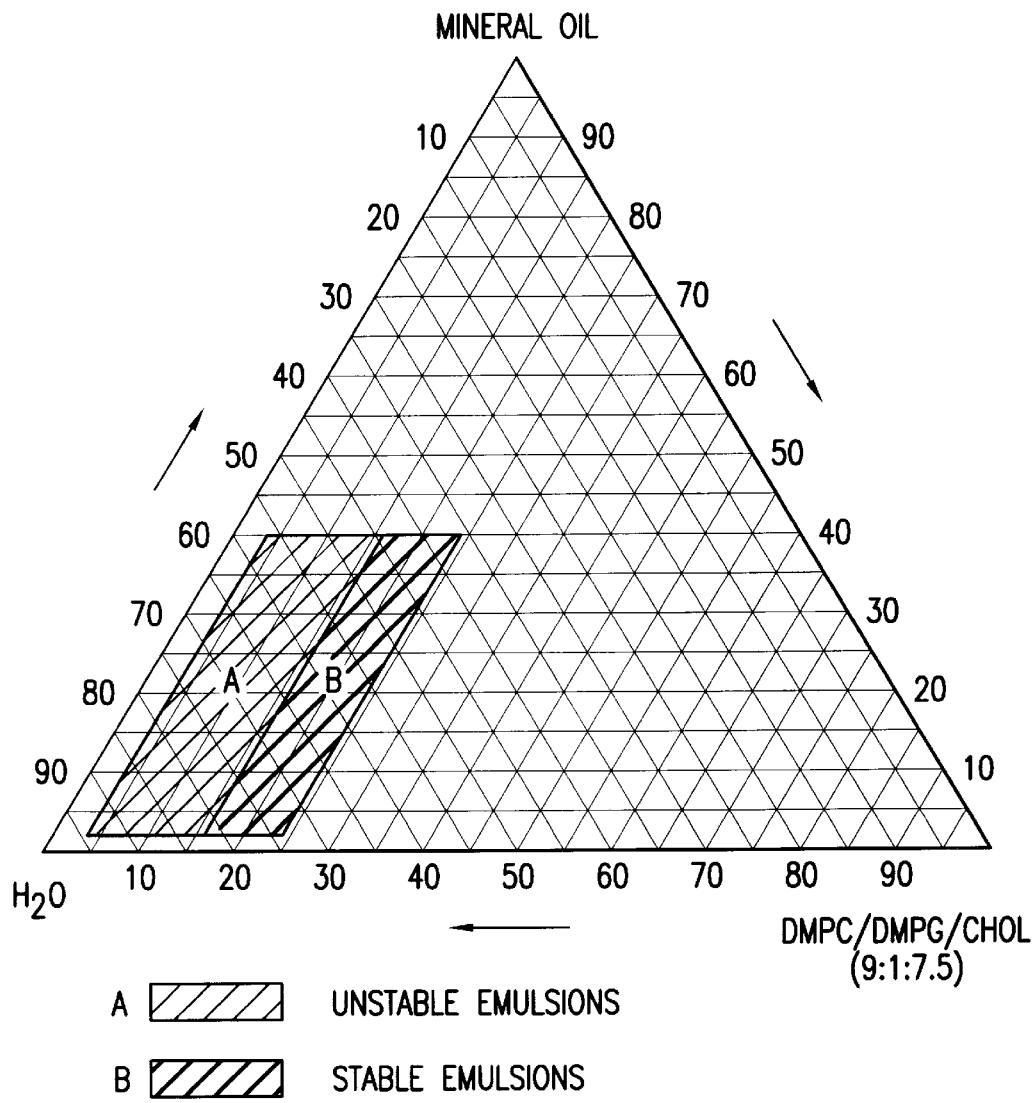
FIG. 12 is a phase diagram showing the ratios of mineral oil, water, and phospholipid contained in liposomes which form stable and unstable emulsions.

As shown in Table 2, concentrations of liposomes which resulted in >100 mM phospholipid in the total emulsion imparted stability to the emulsion as measured in terms of separation of the emulsion. Increasing the percentage of oil also provided enchanced stability although this effect is substantially less dramatic. Only within certain ranges is an emulsion formed at all; at 150 mM phospholipid, the preparation is so thick that dispersion in mineral oil cannot be successfully maintained; the oil droplets cannot remain uncontiguous at high concentrations of mineral oil. FIG. 12 shows these results graphically. Cross-hatched area B provides a range of stable emulsions; cross-hatched area A indicates regions in which the emulsions are unstable and the remaining portion of the diagram represents ratios of components in which emulsions cannot successfully be formed.

What is claimed is:

1. A pharmaceutical or veterinary formulation which comprises a stable oil-in-water emulsion having a continuous water phase and a discontinuous oil phase and containing, as sole stabilizing agent, smectic mesophase vesicles and disintegrated forms thereof, wherein said vesicles encapsulate at least one therapeutically active ingredient and provide 90 mM–140 mM amphiphile in said composition.

2. The composition of claim 1 wherein said amphiphile comprises a phospholipid.

3. The composition of claim 2 wherein the phospholipid comprises DMPG and/or DMPC.

4. The composition of claim 1 wherein said oil phase comprises mineral oil, squalene, peanut oil, vegetable oil, or silicone oil.

5. The composition of claim 1 wherein the water phase is water per se, phosphate buffered saline, saline, or Ringer's solution.

6. The composition of claim 1 wherein the therapeutically active ingredient is an antigen.

7. The composition of claim 6 wherein the antigen is a prostate-specific antigen or a tumor associated antigen.

8. The composition of claim 6 which further contains an adjuvant.

9. The composition of claim 1 wherein from about 20% to about 50% of said vesicles are in disintegrated form.

10. A method to elicit an immune response in a subject which method comprises administering to said subject an amount of the composition of claim 6 sufficient to elicit an immune response to said immunogen.

11. The method of claim 10 wherein said immune response comprises production of antibodies to said immunogen.

12. The method of claim 10 wherein said immune response comprises a cellular immune response.

13. The method of claim 12 wherein said immune response further comprises production of antibodies to said immunogen.

14. A method to prepare an immunogenic formulation which method comprises admixing, by supplying shear forces, an aqueous suspension of smectic mesophase vesicles comprising at least one immunogen and at least one amphiphile sufficient to provide 90 mM–140 mM amphiphile in said composition, with a sufficient quantity of an oil phase to form said formulation as a stable emulsion.

15. The method of claim 14 wherein the ratio of suspension to oil phase is 8:1 to 12:1.

* * * * *